United States Patent [19]
Mackey

[11] Patent Number: 5,931,835
[45] Date of Patent: Aug. 3, 1999

[54] RADIO FREQUENCY ENERGY DELIVERY SYSTEM FOR MULTIPOLAR ELECTRODE CATHETERS

[75] Inventor: Sean Mackey, Sunneyvale, Calif.

[73] Assignee: C. R. Bard, Murray Hill, N.J.

[21] Appl. No.: 08/874,958

[22] Filed: Jun. 13, 1997

Related U.S. Application Data

[62] Division of application No. 08/569,771, Dec. 8, 1995, Pat. No. 5,837,001.

[51] Int. Cl.$^6$ .................................................. A61B 17/36
[52] U.S. Cl. .............................................. 606/34; 607/102
[58] Field of Search ................................. 606/30, 31, 34, 606/38, 42; 607/101, 102, 148

[56] References Cited

U.S. PATENT DOCUMENTS

| | | |
|---|---|---|
| 3,614,521 | 10/1971 | Brueschke . |
| 3,830,223 | 8/1974 | Beretsky et al. . |
| 3,978,470 | 8/1976 | McGuire . |
| 4,016,886 | 4/1977 | Doss et al. . |
| 4,095,602 | 6/1978 | Leveen . |
| 4,365,639 | 12/1982 | Goldreyer . |
| 4,510,937 | 4/1985 | Rogers . |
| 4,817,608 | 4/1989 | Shapland et al. . |
| 4,869,248 | 9/1989 | Narula . |
| 4,940,064 | 7/1990 | Desai . |
| 5,057,105 | 10/1991 | Malone et al. . |
| 5,122,137 | 6/1992 | Lennox . |
| 5,233,515 | 8/1993 | Cosman . |
| 5,239,999 | 8/1993 | Imran . |
| 5,249,585 | 10/1993 | Turner et al. . |
| 5,304,214 | 4/1994 | DeFord et al. . |
| 5,341,807 | 8/1994 | Nardello . |
| 5,366,443 | 11/1994 | Eggers et al. . |
| 5,370,644 | 12/1994 | Langberg . |
| 5,383,917 | 1/1995 | Desai et al. . |
| 5,433,198 | 7/1995 | Desai .......................................... 607/9 |
| 5,433,740 | 7/1995 | Yamaguchi . |
| 5,443,470 | 8/1995 | Stern et al. . |
| 5,454,370 | 10/1995 | Avitall . |
| 5,540,681 | 7/1996 | Strul et al. . |

(List continued on next page.)

FOREIGN PATENT DOCUMENTS

| | | |
|---|---|---|
| WO 94/10922 | 5/1994 | WIPO . |
| WO 95/09576 | 4/1995 | WIPO . |
| WO 95/10321 | 4/1995 | WIPO . |
| WO 95/25472 | 9/1995 | WIPO . |

OTHER PUBLICATIONS

Haissaguerre et al., Journal of Cardiovascular Electrophysiology, 5(12):1045–1052, 1994.
Mackey et al., 65th Scientific Sessions, 62:104488, 1992.
Nardella, SPIE–Catheter–Based Sensing and Imaging Technology, 1068:42–49, 1989.
PCT International Search Report, May 20, 1997 (4 pages).

*Primary Examiner*—Francis J. Jaworski
*Attorney, Agent, or Firm*—Darby & Darby

[57] ABSTRACT

A radio-frequency ablation system is disclosed in which the power, voltage, or temperature delivered to multiple electrodes may be dynamically controlled, and in which the electrodes may be simultaneously energized in phase with each other to achieve a desired lesion pattern. The system comprises a multiple electrode ablation catheter, each electrode having a temperature sensor operatively associated therewith. Each electrode is energized by its own RF amplifier, and all of the electrodes are driven in phase with each other by a common sine wave oscillator. A feedback network controls the degree of amplification of the separate RF amplifiers. According to a further aspect of the invention, a modular power supply arrangement is disclosed which is configurable to dynamically control the power, voltage, or temperature delivered to multiple electrodes of a multipolar ablation device. An arbitrary number of electrodes may be simultaneously energized in phase with each other to achieve a desired lesion pattern using the modular power supply by providing a sufficient number of removable modules.

16 Claims, 5 Drawing Sheets

U.S. PATENT DOCUMENTS

| | | |
|---|---|---|
| 5,540,684 | 7/1996 | Hassler, Jr. . |
| 5,542,916 | 8/1996 | Hirsch et al. . |
| 5,558,672 | 9/1996 | Edwards et al. . |
| 5,569,241 | 10/1996 | Edwards . |
| 5,573,533 | 11/1996 | Strul . |
| 5,584,830 | 12/1996 | Ladd et al. . |
| 5,599,345 | 2/1997 | Edwards et al. . |
| 5,620,481 | 4/1997 | DeSai et al. . |
| 5,702,386 | 12/1997 | Stern et al. ................................ 606/34 |

RADIO FREQUENCY ENERGY DELIVERY SYSTEM FOR MULTIPOLAR ELECTRODE CATHETERS

This is a division, of application Ser. No. 08/569,771, filed Dec. 8, 1995 and now U.S. Pat. No. 5,837,001.

FIELD OF THE INVENTION

This invention relates to electrode catheters and, in particular, to a power supply arrangement for simultaneously delivering single-phase energy to multiple electrodes of an electrode catheter.

BACKGROUND OF THE INVENTION

Cardiac dysrhythmias are commonly known as irregular heart beats or racing heart. Two such heart rhythm irregularities are the Wolff-Parkinson-White syndrome and AV nodal reentrant tachycardia. These conditions are caused by an extraneous strand of muscle fiber in the heart that provides an abnormal short-circuit pathway for electric impulses normally existing in the heart. For example, in one type of Wolff-Parkinson-White syndrome, the accessory pathway causes the electric impulses that normally travel from the upper to the lower chamber of the heart to be fed back to the upper chamber. Another common type of cardiac dysrhythmia is ventricular tachycardia (VT), which may be a complication of a heart attack or reduction of blood supply to an area of heart muscle. This latter type of cardiac dysrhythmia is a life-threatening arrhythmia.

Atrial fibrillation (AF) is the most commonly occurring type of arrhythmia. It is associated with increased morbidity and mortality due to a higher incidence of thromboembolic events and hemodynamic compromise. In patients with disabling drug resistant AF, the ventricular response can be controlled by catheter ablation or modification of the atrioventricular (AV) nodal region, but this procedure is palliative since AF and its related risks are persistent. Pacemakers may be used to prevent recurrence of paroxysmal AF by either preventing the sinus bradycardia that triggers AF or reducing the interatrial conduction delay.

Non-surgical procedures such as management with drugs are favored in the treatment of cardiac dysrhythmias. However, some arrhythmias are not treatable with drugs, for example, disabling drug resistant AF, and have previously required surgery. According to these procedures, various incisions are made in the heart to block conduction pathways and thus divide the atrial area available for multiple wavelet reentry and abolish the arrhythmia. Alternatively, an Automatic Implantable Cardioverter/Defibrillator (AICD) can be surgically implanted into the patient, as described in U.S. Pat. No. 4,817,608 to Shapland et al. While these surgical procedures can be curative, they are associated with increased morbidity and mortality rates, and are extremely expensive. Even the use of an AICD requires major surgical intervention. However, patients of advanced age or illness, for example, cannot tolerate invasive surgery to excise the tachycardia focus which causes dysrhythmias.

Non-surgical, minimally invasive techniques have been developed which are used to locate cardiac regions responsible for tachycardia, and also to disable the short-circuit function of these areas. According to these techniques, electrical energy shocks are applied to the endomyocardium to ablate cardiac tissue in the arrhythmogenic regions and produce scars which interrupt the reentrant conduction pathways. The regions to be ablated are usually first determined by endocardiac mapping techniques. Mapping typically involves percutaneously introducing an electrode catheter into the patient, passing the electrode catheter through a blood vessel (e.g. the femoral vein or aorta) and into an endocardiac site (e.g., the atrium or ventricle of the heart), and inducing a tachycardia so that a continuous, simultaneous recording can be made with a multichannel recorder at each of several different endocardiac positions. When a tachycardial focus is located, as indicated in the electrocardiogram recording, it is marked by means of a fluoroscopic image so that cardiac arrhythmias at the located site can be ablated. A conventional electrode catheter provides electrical energy shocks to the tissue adjacent the electrode to create a lesion in the tissue. One or more suitably positioned lesions will create a region of necrotic tissue which will disable the malfunction caused by the tachycardial focus.

Conventional catheter ablation techniques have used catheters each having a single electrode fitted at its tip as one electrical pole. The other electrical pole is conventionally provided by a backplate in contact with a patient's external body part to form a capacitive coupling of the ablation energy source (DC, laser, RF, etc.). Other ablation catheters are known in which multiple electrodes are provided, such as the catheters disclosed in U.S. Pat. Nos. 5,239,999 to Imran, and 4,940,064 and 5,383,917, both to Desai.

Ablation is effected by applying energy to the catheter electrodes once the electrodes are in contact with the cardiac tissue. The energy can be, for example, RF, DC, ultrasound, microwave, or laser radiation. As between RF and DC ablation techniques, RF ablation is preferable because it does not require that the patient be anesthetized, and it produces more circumscribed and discrete lesions. Further, it avoids injury that may be caused by high voltages, for example, DC shock. When RF energy is delivered between the distal tip of a standard electrode catheter and a backplate, there is a localized RF heating effect. This creates a well-defined, discrete lesion slightly larger than the tip electrode.

The small size of the lesions produced by RF ablation has been perceived as one of the limitations of this technique. Unless the electrode has a large contact region, the lesion created by the simple RF technique delivered through a standard electrode catheter may not be large enough to ablate enough tissue to block ventricular tachycardia, for example, because the electrode tip area is usually only about 0.3 $mm^2$ and the exit site of VT is typically only locatable to within 4–8 $cm^2$ of the earliest site recorded by the endocardiac mapping catheter. Also, attempts have been made to provide an elongated electrode six, eight, ten or even twelve millimeters in length to cause longer lesions, and to allow more power to be delivered to the tissue. However, flexibility of the tips of such catheters is reduced, and a stiffer catheter tip increases the risk of myocardial wall perforation, which in turn increases the morbidity rate of ablation procedures using such catheters.

Several other techniques have been implemented to produce larger and deeper lesions, including the use of different energy sources such as ultrasound, microwave, and laser. Other methods include using a saline-perfused catheter tip to cool the electrode/tissue interface, allowing more power to be delivered.

One particular approach to increasing the size of the lesion is disclosed in U.S. Pat. No. 4,940,064 to Desai. A retractable array of four orthogonal electrodes surrounds a central tip electrode and is powered by a conventional RF power source. This array was found to produce an unsatisfactory lesion pattern (in the form of a plus "+" sign) because substantial areas between the electrodes remained unablated, and the increase of power to the electrodes only resulted in charring of the tissues and early fouling of the electrodes by coagulum formation. As a solution, Desai et al. proposed in U.S. Pat. No. 5,383,917 the use of a multi-phase power source to electrically drive the peripheral electrodes out of phase with respect to adjacent electrodes to create an electric potential between adjacent peripheral electrodes and thereby cause ablation in the regions between those adjacent electrodes (that is, lesions which connect the tips of the plus "+" pattern to one another). This solution dispenses with the use of an external return or passive electrode because ground potential is provided at the central tip electrode, but poses constraints on the dimensions of the electrodes for satisfactory operation, and does not produce a continuous, linear lesion among or between the electrodes. See col. 8, lines 19–30 of U.S. Pat. No. 5,383,917.

In another approach, a series of electrodes were arranged along a catheter shaft to demonstrate the feasibility of catheter ablation of typical human AF by the sequential application of radiofrequency energy in a system using a backplate. Haissaguerre, et al., "*Successful Catheter Ablation of Atrial Fibrillation,* " *J. Cardiovascular Electrophysiology,* 1994, Vol. 12, No. 5:1045–1052. While the investigators in this study cured the AF in the patient, they were unable to confirm whether the lesions produced at the site of each electrode joined together to form a continuous lesion.

What is needed in the art and has heretofore not been available is a power supply arrangement for independently and controllably driving a multiplicity of electrodes spaced along the distal end of a cardiac ablation catheter. Also needed in the art is an ablation system which incorporates such a power supply arrangement with an ablation catheter so that continuous, linear ablation lesions of a predetermined contour can be formed in the endomyocardium.

OBJECTS OF THE INVENTION

Accordingly, it is a general object of the present invention to improve catheter ablations.

It is an object of the present invention to improve cardiac catheter ablations.

It is also an object of the present invention to improve power supplies for use in catheter ablation procedures.

It is another object of the present invention to control the contour of lesions created by RF catheter ablations including both the length and depth of such lesions.

It is yet another object of the present invention to improve the efficiency of RF catheter ablation procedures.

It is yet another object of the present invention to treat ventricular tachycardia by improved RF catheter ablations.

It is yet a further object of the present invention to treat atrial fibrillation by improved RF catheter ablations.

These and other objects are accomplished by simultaneous, parallel application of a single-phase RF power source to multiple poles of an electrode catheter such that the voltage, power, or temperature can be controlled as the ablation procedure proceeds.

SUMMARY OF THE INVENTION

According to one aspect of the invention, a radio-frequency ablation system for biological tissues is provided in which the power, voltage, or temperature delivered to multiple electrodes may be dynamically controlled, and in which the electrodes may be simultaneously energized in phase with each other to achieve a desired lesion pattern.

The system comprises an electrode catheter having a generally longitudinally extending shaft which defines a lumen, and an array of externally conductive, individually connected electrodes arranged in spaced serial relation along the shaft. The electrode catheter further comprises a plurality of temperature sensors each of which is thermally associated with a different electrode in the array to provide a temperature signal representative of the temperature of that electrode. A plurality of RF amplifiers are electrically connected to different electrodes in the array. Each RF amplifier provides drive signals representative of the voltage and current applied to the electrode to which it is connected. A feedback control network is provided with these drive signals along with the temperature signal for the same electrode. in response to the received temperature and drive signals of a particular electrode, the feedback control network provides an amplification signal to each RF amplifier. Also, a RF sine wave oscillator, which has an output that is separately amplified in phase by each of the RF amplifiers in accordance with the amplification signal from the feedback control network for that RF amplifier, is also provided to independently drive each of the electrodes in the array of electrodes in phase with each other.

According to another aspect of the invention, a modular power supply arrangement for a multipolar ablation device is provided. The modular power supply arrangement comprises a mother board including one or more receptacles adapted to receive a module, a sine wave oscillator which has an output electrically connected to the receptacle, and a feedback control network which (1) receives input signals from the module in the receptacle, (2) processes the input signals, and (3) provides an amplification signal which is responsive to the input signals to that module. The modular power supply arrangement further comprises at least one module removably connected to the receptacle. In its simplest form, the module includes a RF amplifier for driving a particular pole of the multipolar ablation device in phase with the oscillator output in accordance with the amplification signal from the feedback control network, and a signal sensor for sensing predetermined operating parameters of the particular pole of the multipolar ablation device and providing the input signals to the feedback control network. Two or more such modules are used to energize multiple electrodes.

Multiple electrodes are controlled by the modular power supply arrangement when multiple receptacles are provided, or when modules which are configured to energize multiple electrodes are provided, or both. According to one modification of the invention, the module may be configured with multiple RF amplifiers, each driving a different pole of a multipolar ablation device in phase with the sine wave oscillator output and in accordance with the amplification signal from the feedback control network. Further, each module according to this modification is configured with a plurality of signal sensors for sensing predetermined operating parameters of the multipolar ablation device and providing the input signals to the feedback control network.

DETAILED DESCRIPTION OF THE PREFERRED EMBODIMENTS

Figure 1:
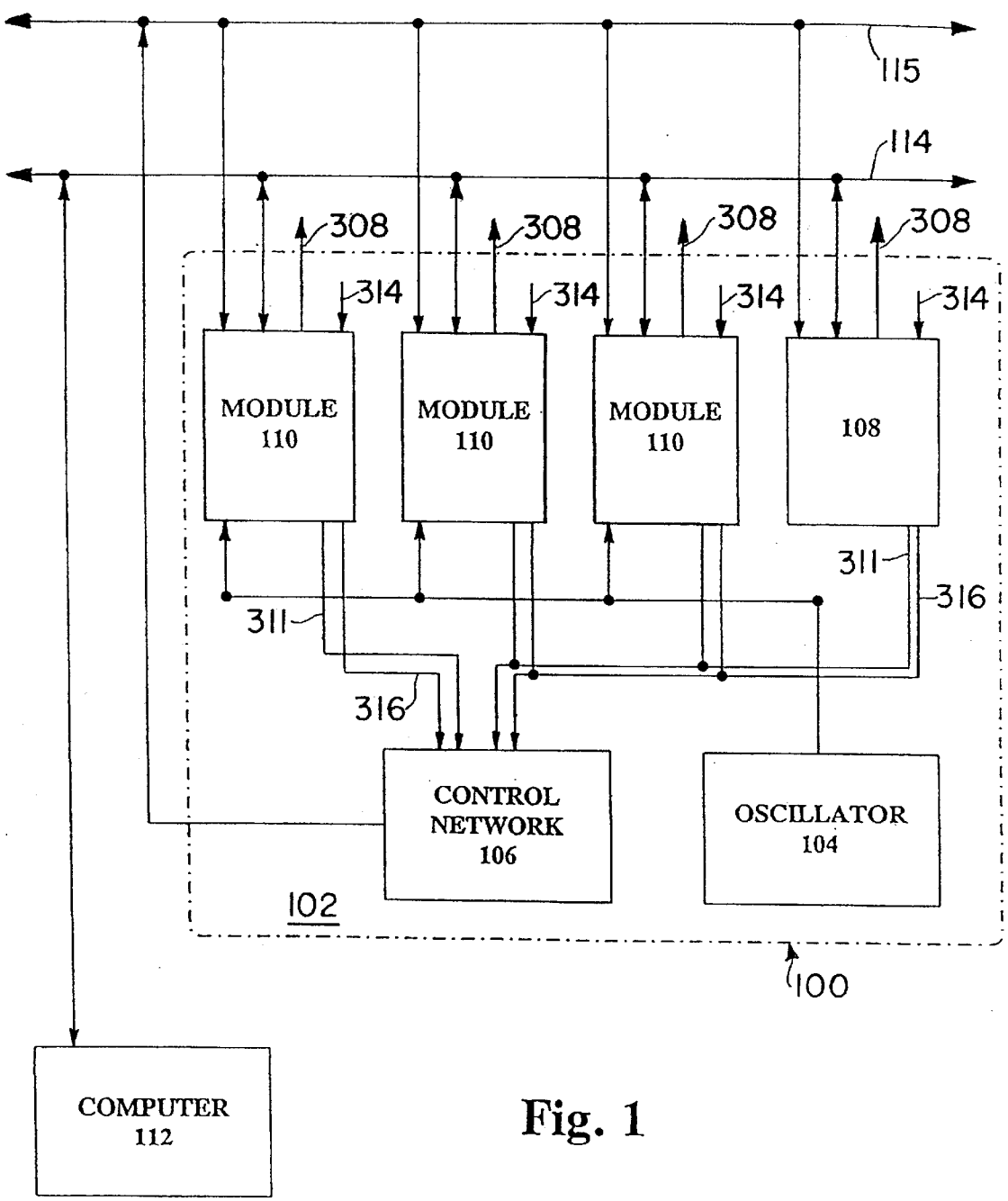
FIG. 1 schematically illustrates a RF power supply arrangement for an ablation catheter according to the invention.

By way of overview and introduction, there is seen in FIG. 1 a schematic illustration of a power supply arrangement 100 according to the present invention which is adapted to maintain constant power, voltage, or temperature at each electrode of a multielectrode catheter. Arrangement 100 is preferably constructed on a mother board 102 and includes a sine wave oscillator 104, a control network 106, and a plurality of receptacles 108 adapted to receive plug-in daughter boards or modules 110. Each daughter board 110 is computer addressable over a bidirectional data and address bus 114, and contains feedback loop control circuitry for individually maintaining one or more electrodes at a constant power, voltage, or temperature. A computer 112 operatively attached to and in signal communication with the bus 114 preferably includes operating software which is adapted to provide control signals to the modules 110 for individually controlling the electrodes of a multielectrode catheter. The computer 112 also preferably includes appropriate input/output features and software for dynamically displaying the current, time, voltage, power, temperature, or impedance of the individual electrodes, or displaying other signals such as electrocardiograms (EKGs).

The sine wave oscillator 104 on the mother board provides a predetermined frequency drive signal in the range of 20 to 500 Khz to each of the modules 110 so that each the RF amplifiers, which are part of the modules 110, in the power supply arrangement 100 is driven in phase with the others. The lower end of the drive signal range (that is, about 20–50 Khz) is conventionally used at a relatively low-amplitude level to determine catheter contact with the endocardium without stimulating the heart as contact measurements are being made. At higher frequencies, the heart is not stimulated at the amplitudes used in the ablation procedure.

Figure 2:
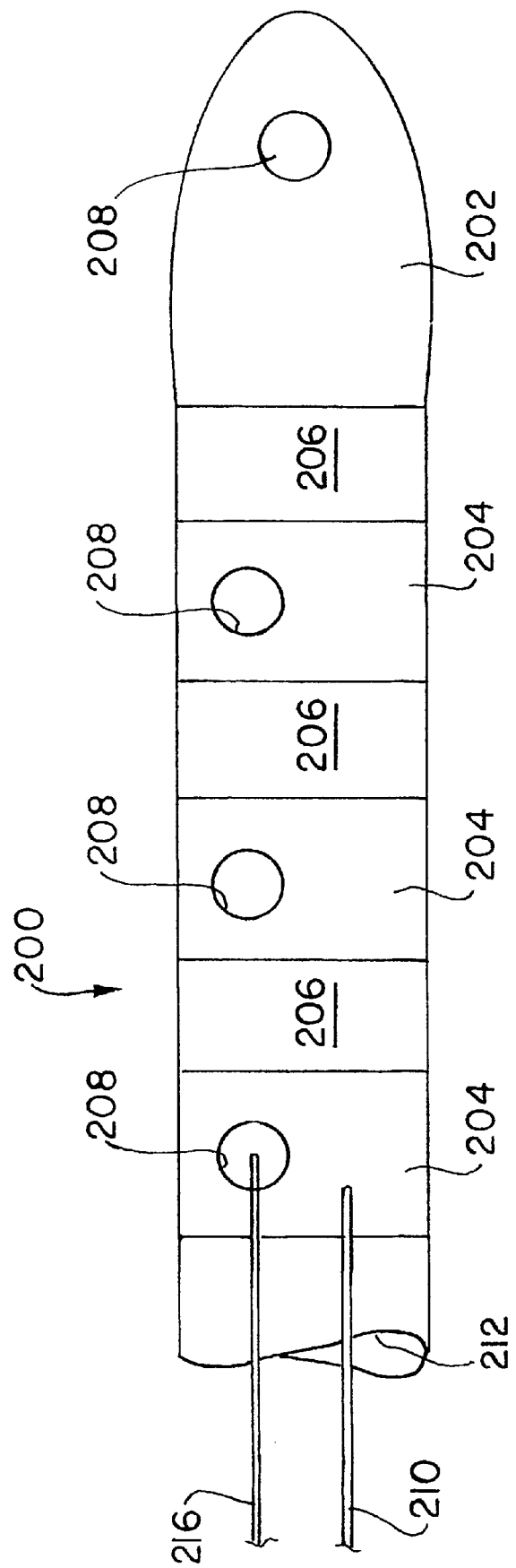
FIG. 2 is a diagrammatic view of the distal end of an ablation catheter which is carrying multiple electrodes and temperature sensors.

The power supply arrangement 100 of FIG. 1 has utility, for example, with medical devices such as catheter 200, the distal end of which is illustrated in FIG. 2. The catheter 200 is an ablation catheter configured with multiple electrodes, serially spaced in an axial direction along the catheter. The catheter 200 is conventionally constructed of an insulative, biocompatable tubing material, and has an outside diameter small enough to pass through a vascular system from an introducer site to a desired cardiac chamber, and has the capability to negotiate the vascular system. In other words, it is sufficiently flexible to be advanced through a tortuous vasculature, yet possesses sufficient column strength to permit its advancement therethrough.

The catheter 200 has a tip electrode 202 which occupies the distal 2–4 mm of the catheter. Conventionally, the tip electrode 202 is made of platinum and is attached directly to the distal end of the catheter 200. Alternatively, a refractive material (not shown) may be interposed between the tip electrode 202 (or the other electrodes) and the catheter 200 to prevent melting of the supporting catheter during and just after ablation energy has been applied to the electrode. In addition, the catheter 200 has externally conductive ring electrodes 204 spaced therealong in serial manner. Three ring electrodes 204 are illustrated in FIG. 2; however, the catheter 200 can have an arbitrarily large number of electrodes. For example, Dr. Michel Haissaguerre has proposed a catheter construction for AF treatment which has thirteen ring electrodes 204 and a single tip electrode 202. The ring electrodes 204 are spaced from each other (and the tip electrode 202) by insulative regions 206, and each can be of an arbitrary axial length. Presently, they are preferably approximately 2 mm in axial length. While the ring electrodes 204 can be spaced 1–3 mm apart, as described in more detail below in connection with an ablation system according to the invention, it is presently preferred that they be spaced 1 mm apart.

Each electrode 202, 204 has a separate conductive lead 210 attached thereto which extends proximally through at least one lumen 212 in the catheter 200 to a connector 214 (not shown). Also, associated with each electrode 202, 204 is a temperature sensor 208 disposed adjacent the electrode for providing an electrical signal indicative of the temperature of the electrode. The temperature sensor 208 can be a thermocouple, thermistor, or resistive thermal device ("RTD"). Each temperature sensor 208 has a conductive lead 216 attached to it which extends proximally to the connector 214. A cable 218 (not shown) houses the electrode and temperature sensor leads 210, 216 between the proximal end of the catheter 200 and the connector 214. The connector mates with a terminal on the module 110.

Figure 3:
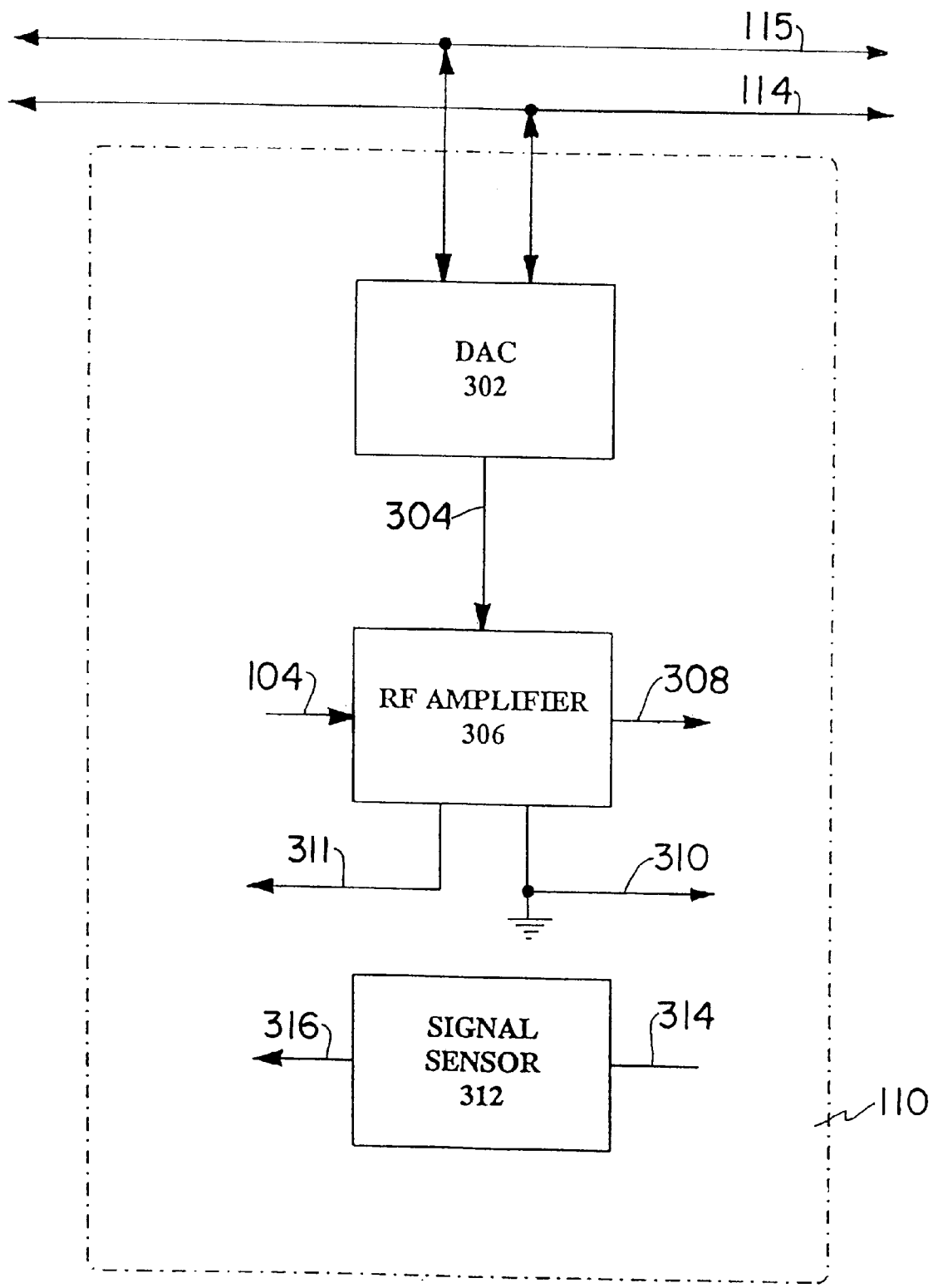
FIG. 3 is a detailed schematic illustration of a module for insertion into the power supply arrangement of FIG. 1, the module being adapted for use with a single electrode.

With reference now to FIG. 3, the circuitry in each module 110 is described.

The module 110 communicates with the computer 112 via the two-way bus 114 via an electrical connection between the module 110 and the receptacle 108 of the mother board 102. A digital-to-analog converter (DAC) 302 is arranged in conventional manner to be addressed by the computer 112, as will be readily understood by those of ordinary skill in this art. In addition, the DAC 302 receives digital signals directly from the control network 106, described below, on leads 115. The DAC 302 converts a digital signal from either the computer 112 or the control network 106 into an analog amplification signal which is latched to an output line 304. The magnitude of the output from a respective DAC 302 will determine the gain, or degree of amplification, of a particular RF amplifier 306. The predetermined or fixed level output from the oscillator 104 is amplified by the variable gain provided by RF amplifier 306 with regard to the feedback signals from an associated electrode 202, 204 so that at least the desired operating parameter (e.g., power, voltage, or temperature) remains constant. There are other functionally equivalent ways of providing an unfaltering control signal to the RF amplifier 306, the use of the DAC 302 being merely illustrative of a presently preferred arrangement. For example, a commercially available digitally controllable potentiometer, such as a sixty-four bit-256 step high-bandwidth potentiometer, can provide direct attenuation of the oscillator signal in response to feedback signals substantially as described above instead of using the DAC 302.

The amplification signal on output line 304 is applied at an input of a RF amplifier 306. The RF amplifier 306 additionally has a high-impedance input for receiving an analog signal from the oscillator 104. The high impedance input of the RF amplifier 306 buffers the oscillator 104 from the load on its high-voltage output line 308, namely, the load presented by one of electrodes 202, 204 before, during, and after an ablation procedure. The RF amplifier provides clean amplification of the sine wave to a level sufficient to drive the electrodes 202, 204 during an ablation procedure, for example. On the other hand, the oscillator 104 provides a relatively distortion free sine wave to each RF amplifier 306 connected to the power supply arrangement 100, and the sine wave received by any one of the RF amplifiers 306 is in phase with the sine wave received by any other of the RF amplifiers 306 that may be connected to the power supply arrangement 100 through a module 110.

The output line 308 of the RF amplifier 306 connects to the electrical lead 210 of a particular one of the electrodes 202, 204 via the conventional connector 214 (not shown). The passive or return electrode, which is disposed on an extremity of the patient, is connected to the low-voltage (ground) output 310 of the RF amplifier 306, preferably through an electrical connection from the mother board 102 to ensure that each of the RF amplifiers 306 connected to the power supply arrangement 100 has a common ground.

Further, the RF amplifier 306 includes sense output lines 311 so that the control network 106 can dynamically determine and monitor the resistance of the tissue being ablated and can responsively adjust the power, voltage, or temperature being delivered to the electrode. The sense lines 311 include a voltage signal representative of the voltage which was applied to the electrode and a voltage signal representative of the current which passed through the tissue, as measured across a known, low resistance (e.g., 1 $\Omega$). This voltage sensing is accomplished in a preferred embodiment by RMS-to-DC converters which convert the detected peak voltage signals, after they have been suitably scaled for the RMS-to-DC converters.

The module 110 further has a signal sensor 312 which filters and amplifies, for example, a relatively low-voltage sensed signals which would be continuously received from the temperature sensors 208 over line 314 assuming that the temperature sensors are thermocouples. If thermistors or RTDs were to be used, it is understood that a wheatstone bridge or other circuitry would be provided to convert a sensed resistance into a voltage signal. In this manner, a clean, sensed voltage signal indicative of the temperature at a particular electrode is obtained and output on line 316. The input line 314 of the signal sensor 312 connects to the temperature sensor lead 216 of a particular one of the electrodes 202, 204 via a conventional connector 214 (not shown). The sensed signal on line 316 is dynamically processed by the control network 106, which, in turn, regulates the power supply 100 so as to maintain constant power, voltage, or temperature at the electrode from which the sensed signal was obtained.

Preferably, a signal sensor 312 is provided for each temperature sensor 208. However, a single signal sensor 312a may be associated with the temperature sensors 208 which are thermally associated with a different electrodes 202, 204 of the catheter 200 or other medical device, by circuitry configured to multiplex the outputs of several temperature sensors 208 into the signal sensor 312a. Such an arrangement is functionally identical to providing a signal sensor 312 for each electrode/temperature sensor pair. Further, the shared signal sensor 312a may be provided on the mother board 102 to reduce the number of components on any one module 110 (or module 110a, described next).

The module of FIG. 3 is configured to provide high-voltage output signals to a single ablation electrode on output line 308, and receive sensed signals from a temperature sensor 208 associated with the same electrode on input line 314. In the power supply arrangement of FIG. 1, four receptacles 108 are illustrated, each one adapted to receive a module 110. Thus, four modules as in FIG. 3 can be plugged into the mother board 102 to enable the power, voltage, or temperature of four electrodes to be dynamically controlled, and the electrodes simultaneously energized in phase with each other to achieve a desired lesion pattern. The invention is not limited to the use of four such modules, as additional receptacles 108 may be provided for any desired number of electrodes.

Figure 4:
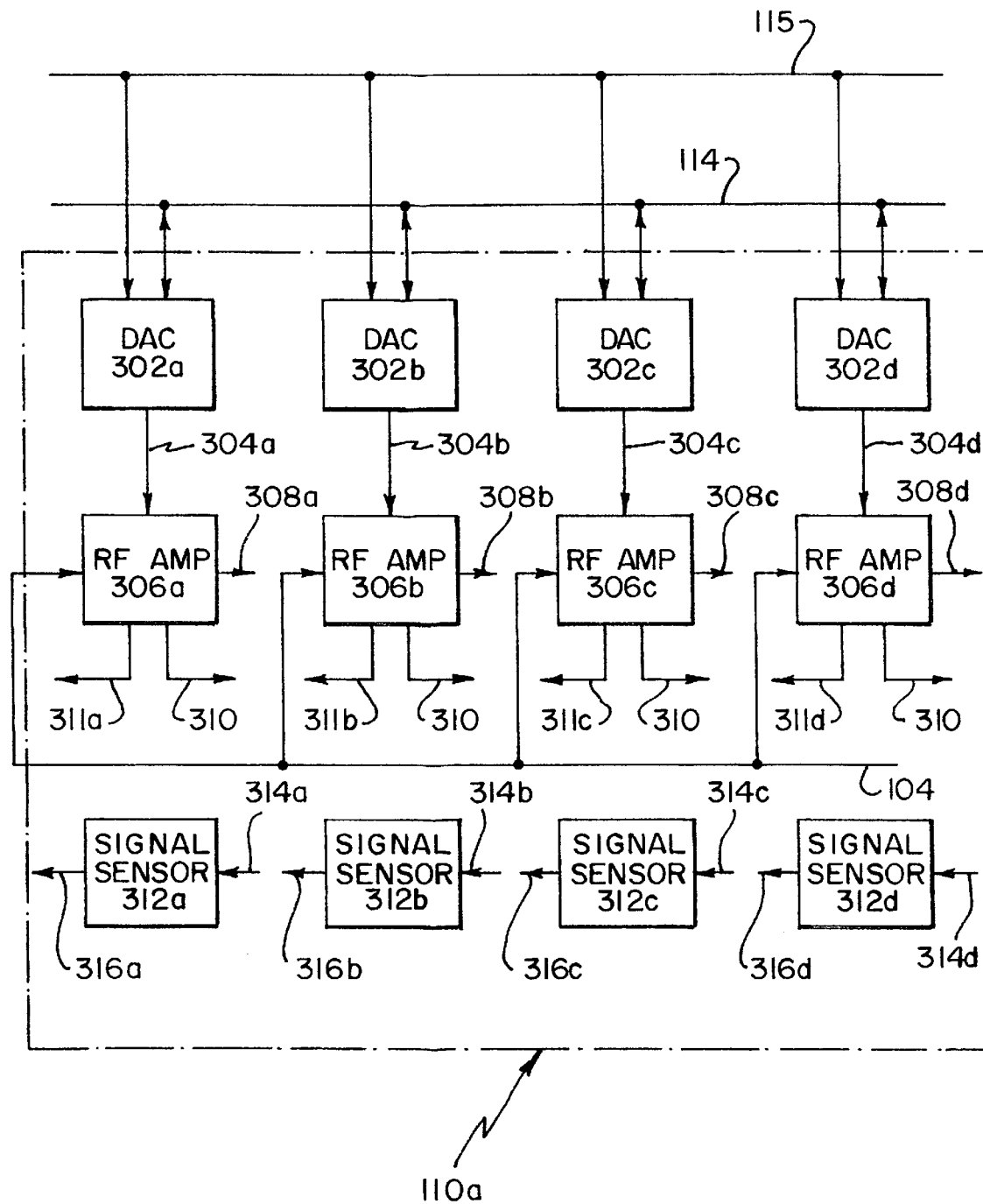
FIG. 4 is a detailed schematic illustration of a modified module for insertion into the power supply arrangement of FIG. 1, the modified module being adapted for use with four electrodes.

Further, each module 110 need not be limited to providing and receiving signals from a single electrode/temperature sensor pair. With reference now to FIG. 4, a modified module 110a is illustrated in which features common to FIG. 3 have been illustrated with corresponding reference numerals. When inserted into the mother board 102, a single module 110a permits signals to be simultaneously provided to and received from four electrode/temperature sensor pairs. Thus, RF amplifier 306a can apply ablation energy over output line 308a in accordance with the amplification signals from the DAC 302a on its output line 304a, while RF amplifier 306b can simultaneously apply ablation energy over output line 308b according to the amplification signals it receives over line 304b just as if two modules 110 were plugged into separate receptacles 108 on the mother board 102. However, the module 110a has input and output lines for two more electrodes. Thus, a single module 110a plugged into a receptacle 108 can accommodate as many electrodes as four modules 110 (which would occupy all of the receptacles 108 in FIG. 1). If four modules 110a were plugged into the four-receptacle arrangement of FIG. 1, then up to sixteen electrodes may be simultaneously energized and dynamically controlled. Combinations of modules 110 and 110a are also possible, as well as the connection of modules having circuitry for additional or fewer electrode/temperature sensor pairs. The mother board 102 preferably includes multipin receptacles 108 which are adapted to receive modules that can accommodate between 1 and 10 electrode/temperature sensor pairs. Because RF amplifiers 306 have high input impedance, an arbitrary number of RF amplifiers can be connected to the oscillator 104, within practical limits, to support a catheter with the same number of electrodes, with the RF energy being delivered to each of the electrodes in phase with each other.

According to an aspect of the invention, a modular power supply arrangement 100 is provided which is expandable merely by inserting additional daughter boards or modules 110 into receptacles 108. A basic module 110 can be inserted into each receptacle 108, or a more complex module 110a, etc. can be inserted into one or more receptacles. By this arrangement, circuitry sufficient for the intended catheter 200 or other medical device can be installed on an as-needed basis. Further, older modules can be readily replaced or substituted with newer ones with great facility, when and as such improvements are made.

Figure 5:
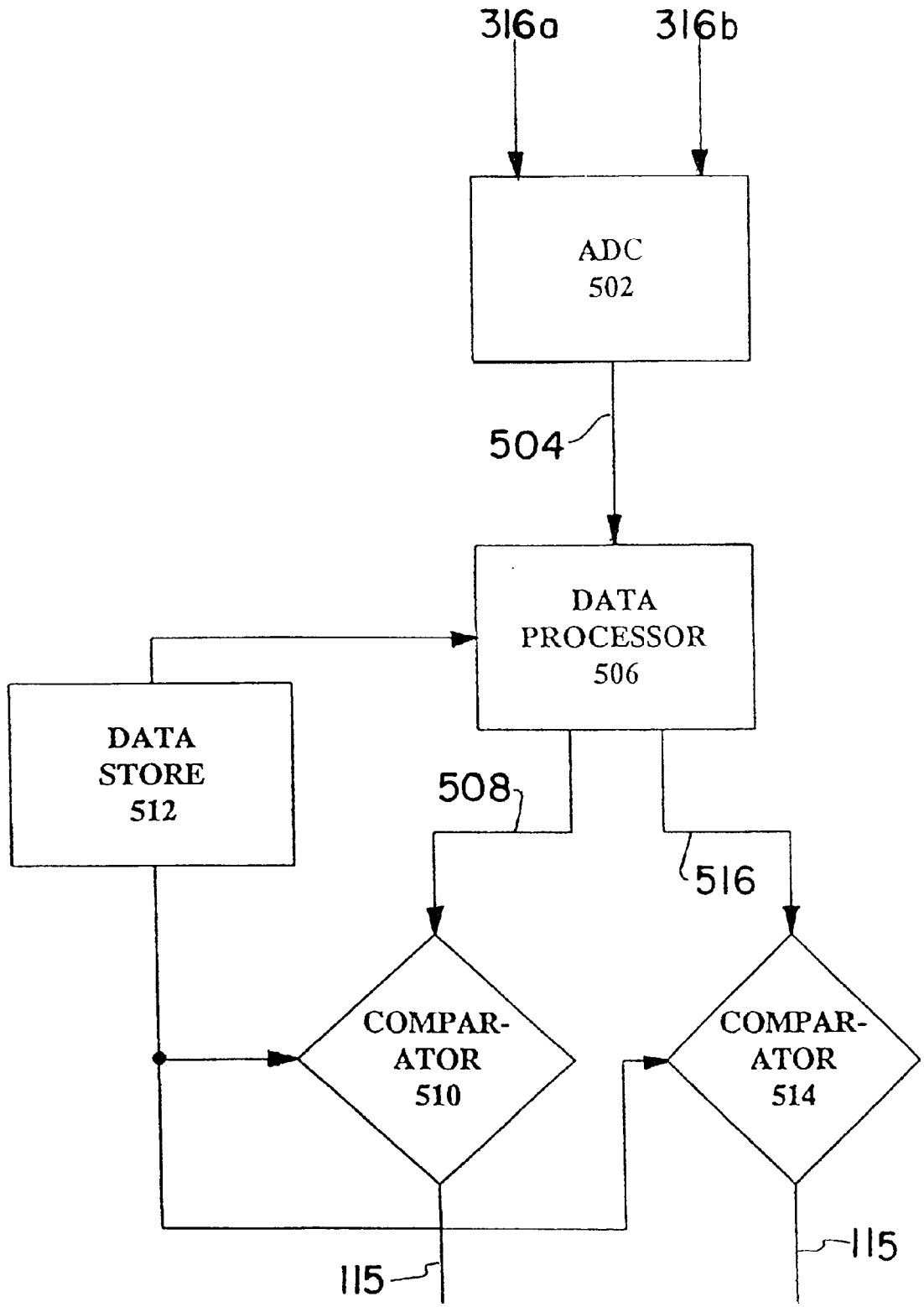
FIG. 5 is a detailed schematic illustration of the control network of FIG. 1.

Each RF amplifier provides a fixed level of amplification based on the magnitude of the amplification signal latched onto the output line 304 of the DAC 302. The amplification signal latched onto output line 304 at any moment can originate either at the computer console 112 or the control network 106, shown in greater detail in FIG. 5. The control network 106 comprises a decision-based feedback loop which dynamically monitors the amplified and filtered sensed signals 316 from the temperature sensor 208 of a particular electrode, and provides signals to the DAC 302 for that electrode via line 115 which controls the degree of RF amplification by that electrode's RF amplifier 306. Likewise, the control network 106 comprises a decision-based feedback loop which dynamically monitors the sense output lines 311 from the RMS-to-DC converters associated with a particular RF amplifier 306, and similarly provides control signals on line 115 to control that electrode's RF amplifier 306. In the preferred embodiment, the control network 106 includes both software and hardware. The software portions of the control network 106 can be implemented on the computer 112.

The control network 106 clocks in the output signals 316 from the signal sensors 312 and from the RMS-to-DC converters on sense output lines 311 on board each module 110 as separate channels to an analog-to-digital converter (ADC) 502. These signals on lines 311, 316 comprise the operating parameters of the multipolar ablation device, for example, the catheter 200. Because the clock (not shown) can run substantially faster than the time constant of the system, which is limited by the speed of the temperature sensors and the tissue itself, the ADC 502 processes the signals 316 faster than they can change, which is effectively a continuous processing of the signals from each of the electrodes of the ablation catheter 200 or other medical device. The ADC 502 multiplexes these signals into a single digital data stream representative of each of the three detected voltages for each electrode/temperature sensor pairs for further processing in the digital domain. The digital data are then processed by data processor 506 which determines the instantaneous tissue impedance R and temperature of the electrode at the temperature sensor 208. The instantaneous tissue impedance R is determined by dividing the sensed voltage applied to the electrode by the current through the electrode. This requires that the current through the electrode be calculated first. This current is determined by the data processor 506 by dividing the voltage signal which is representative of the current that passed through the tissue by the known resistance value, which value is retrievable, for example, from a computeraddressable data store such as data store 512. The true tissue impedance R is the result of these calculations after suitable scaling according to a calibrated scale, which may be readily determined for the particular device being used as understood by those of ordinary skill in this art. The instantaneous temperature is readily determined from the voltage signal from converted signal on the output line 504 of the ADC 502. If the temperature sensor 208 is a thermocouple, the temperature is linearly related to the sensed DC voltage according to the particular characteristics of the device being used, which can be calibrated and which calibration can be stored in a data store, such as the data store 512 for use by the data processor 506, as understood by those skilled in the art. If the temperature sensor 208 is a thermistor, then each increase/decrease in temperature is linearly related to each decrease/increase in resistance, respectively. Again, the particular thermistor under consideration can be calibrated and the calibration data can be stored in the data store 512.

The data processor 506 provides the determined tissue impedance R to a comparator 510, for example, along output line 508. The comparator compares the impedance R to data from a data store 512 to determine whether the impedance has risen abruptly, or whether it is greater than a prescribed threshold value. As understood by those skilled in the art, when tissue impedance exceeds a predetermined value which depends on the length of the electrode and whether the electrodes are being driven simultaneously (e.g. 200 Ω for a 4 mm electrode and approximately 400 to 500 Ω for a 2 mm electrode), there may be blood coagulation or protein deposits on the electrode. Conventional RF ablation schemes produce early impedance rises at the power supply due to efficient necrosis of tissues and possibly early coagulum formation at the electrodes. The formation of coagulum has the effect of restricting the current flow through the endomyocardium and limiting the depth of lesion formation therein. When coagulation begins, the impedance tends to rise abruptly above the predetermined value for the chosen electrode length. Accordingly, if the tissue impedance R has either risen abruptly or surpassed a prescribed threshold value, for example, 400 Ω, then the input lines to the DAC 302 for a particular electrode at which the impedance was measured are enabled, and a reduced magnitude drive signal can applied to the DAC 302 so that the magnitude of the amplification signal latched on the output line 304 is reduced, whereby the ablation energy delivered to the electrodes on line 308 is reduced. The DAC 302 can be enabled by a direct address write, or by addressing it in conventional manner. On the other hand, if neither of these conditions are established, then either the previous drive signal is reapplied to an enabled DAC 302, or no action is taken. The particular impedance value at which coagulum formation might commence may be set by the operator or adjusted a program operating on a computer based on the identification of the particular catheter being used, or its operative characteristics (electrode length, electrode diameter, electrode spacing, electrode material, etc.).

The output of comparator 510 is connected to line 115 and can provide a reduced magnitude drive signal by decrementing the previous drive signal which may be stored in the data store 512 and enabling the input lines of the DAC 302. Alternatively, an increased magnitude drive signal can be applied to the electrodes if desired or necessary, for example, by incrementing the previous drive signal and enabling the input lines of the DAC 302.

Similarly, the data processor 506 provides the determined temperature to a comparator 514, for example, along output line 516. The comparator compares the temperature to data in, for example, the data store 512 to determine whether the temperature has risen abruptly, or whether it is greater than a prescribed threshold value. One manner of alleviating the problem of early coagulum formation at the electrodes is by closely regulating the ablation temperature to just below approximately 80° C. This also helps to produce larger and deeper lesions with more uniformity. Accordingly, if the temperature has either risen abruptly or surpassed a prescribed threshold value, for example, 80° C., then the ablation energy delivered to the electrodes on line 308 is reduced as previously described. On the other hand, if neither of these conditions are established, then either the previous drive signal is reapplied to an enabled DAC 302, or no action is taken.

In operation, the power supply arrangement 100 is configurable at the computer console 112 in any one of a constant voltage, power, or temperature mode to provide energy for an ablation procedure to the catheter 200 or other medical device. The control network 106 continuously monitors and dynamically alters the power or voltage delivered or the temperature sensed at each of the electrodes, depending on the selected mode, so that the electrodes can be simultaneously energized yet be dynamically controlled so that the power, voltage, or operating temperature remains constant.

In the constant voltage mode, a user-set voltage is output to each of the electrodes 202, 204 and separately maintained throughout the ablation. This permits the operator to control the depth of lesion formation at each electrode and provides a vehicle for focusing the RF energy to produce a lesion that is, for instance, deeper at the proximal end than at the distal end. Alternatively, this mode of operation permits a more uniform lesion to be produced, even if electrodes of different dimensions are being used, such as a 4 mm tip electrode 202 and 2 mm ring electrodes 204. Electrodes of different dimensions, when driven with the same potential, will have differing power density distributions across them. Thus, the larger electrode will have a greater power density than the smaller electrode if driven at the same potential. However, the power supply arrangement 100 accounts for these discrepancies in the constant voltage mode to permit a comparatively more uniform lesion profile than achievable in known present ablation catheter systems.

In the constant power mode, the tissue impedance R is dynamically monitored and the voltage applied to the electrodes 202, 204 varied with changes in tissue impedance R to maintain a constant power level delivered at the site of each electrode. As in the constant voltage mode, lesions of arbitrary profile can be created. Tissue impedance is monitored at the operating frequency of the sine wave oscillator 104. Because tissue impedance is typically higher than blood impedance, particularly in the 20–50 Khz range being used for sensing tissue contact, the sensed impedance data for each of the electrodes may be used to determine whether sufficiently conductive contact has been made between the electrodes and the myocardial wall. The catheter can be repositioned in the event that one or more of the electrodes are determined to be in less-than-desirable contact with the myocardium. The software executed on the computer 112 can be adapted to make this determination and to suggest catheter repositioning in response thereto, or this determination can be made by the operator after reviewing the impedance data on the screen of the computer console 112.

It is noteworthy that there may be a rise in the tissue impedance R adjacent the more proximal electrodes on the catheter 200 as compared to the more distal electrodes. This is not detectable by overall tissue impedance measurements which treat each electrode as a separate impedance in parallel with the other electrodes and thereby masks the individual impedances at each electrode. Therefore, an impedance rise at one of these electrodes would not result in an overall rise of the parallel impedances. Nevertheless, this impedance rise could cause adhesion of the catheter to myocardial tissue that could be hazardous. However, the present invention allows monitoring of the impedance and control of the energy delivery at each electrode to avoid this effect, or to terminate ablation at the tissue site of the electrode for which an impedance rise was detected. The invention therefore permits a single ablation of a larger area than possible with a single electrode or multiple pole electrode catheter that lacks the inventive features described above, because several poles can be operated simultaneously without the inherent problems of a single large electrode.

Finally, in the constant temperature mode, the electrode temperature is dynamically monitored and the output voltage varied to maintain a constant, preset temperature. A closed loop feedback system permits the voltage to each electrode to be dynamically controlled to maintain the temperature at a user-defined level. Thus, any change in impedance due to tissue desiccation, blood coagulation, or charring at the electrode can be accommodated. As a direct result of maintaining the site temperature such that there is no blood coagulation, the potential for thrombus formation or the adhesion of the catheter to the myocardium is reduced. If an undesired temperature is detected at the electrode, the comparator 514 outputs control signals to the DAC 302 to manipulate the output power of the RF amplifier driving that electrode to maintain the sensed tissue temperature below the predetermined temperature. Meanwhile, the RF voltage delivered to the remaining electrodes remains unaffected.

In operation, once the arrhythmogenic site is determined, the power supply arrangement 100 is configured in one of the constant voltage, power, or temperature modes. Then, radio-frequency energy in the range typically of about 250 Khz to 500 Khz is delivered simultaneously to each of the electrodes 202, 204. Energy flows from the catheter 200 through the tissue to a return plate, which is connected to ground via line 310 and is positioned on the patient's skin, thereby completing the electrical circuit. This flow of current to the tissue causes heating. The heating results in the destruction of the tissue near the electrode, and ideally the arrhythmogenic site. If performed successfully, permanent interruption of the arrhythmia occurs and the patient is cured.

The control network 106 continuously monitors and dynamically controls either the power, voltage, or operating temperature of each of the electrodes, depending on the selected mode. The operator can override, record, monitor, or otherwise supervise the procedure via computer console 112.

If any of the electrode conditions exceeds a user-defined impedance or temperature limit, or if impedance or temperature rise too rapidly, the electrode may be automatically deenergized, or it may simply have the energy applied to it attenuated. This prevents or reduces further delivery of RF power to that tissue site, while the remaining poles continue to deliver relatively greater amounts of RF energy. Thus, for example, if one portion of the endomyocardium is sufficiently heated to cause scarring, then only the surrounding tissue adjacent to the remaining poles will have further energy applied.

Preferably, the computer 112 has software loaded in its memory which controls the system 100, for example, using the Microsoft Windows graphical user interface environment. In this manner, a familiar interface is provided to the user which affords access to all of the functions needed to control the ablation system 100. Also, real-time monitoring of the ablation parameters can be displayed graphically for any one of the electrodes, as described in U.S. Pat. No. 5,233,515 to Cosman, the disclosure of which is incorporated by reference as if set forth fully herein, or for all of the electrodes of a multipole catheter such as catheter 200, or some other medical device. Further, all of the data obtained during the procedure can be saved to disk for later retrieval and analysis. The data can be dynamically collected and displayed as well as written to disk for later analysis.

An ablation system according to another aspect of the invention combines a multipole catheter such as catheter 200 or other medical device with the power supply arrangement 100 and a computer such as computer console 112.

A catheter has been constructed with its ring electrodes spaced 1 mm from each other and the tip electrode. Empirical data has demonstrated that approximately 1 mm spacing of 2 mm long ring electrodes promotes the formation of a continuous lesion in the regions between the electrodes when the electrodes are simultaneously energized using in-phase RF energy, without the abrupt temperature effects that have been observed when using electrodes that have been serially spaced over different lengths. The 1 mm spacing thus results in an overlap of power density into the endomyocardial tissue linearly disposed between the serially spaced electrodes (202, 204).

This electrode spacing is believed to produce the phenomenon of "charge crowding" in which the localized impedance of that part of the electrode which is in proximity to another electrode (its edge) appears to be increased by the in-phase energy signal which is being concurrently applied to the adjacent electrodes. This appears to cause a reduction in the power density at the electrode's edge. In any event, a more uniform temperature distribution across the electrode has been observed. This is important because temperature sensors have conventionally been attached to the mid-point of an electrode to gauge its nominal temperature. Thus, such sensors have not measured the exponential rise in temperature which occurs at the electrode edges due to the rise in power density at the electrode edges. As a result, even in systems in which temperature monitoring of the electrodes has been used, blood coagulation and electrode fouling has occurred without the operator being informed of the significant elevation in overall temperature.

An ablation procedure using the foregoing ablation system reduces the time required to complete the treatment because the catheter 200 need only be placed in two or three different locations in the heart. All of the electrodes are energized for approximately one to two minutes. As compared to a sequentially firing method using a multiple pole catheter such as catheter 200, the treatment time is reduced by up to about thirteen minutes for each catheter placement, which may result in an overall time savings of more than one half hour in a typical ablation procedure. On the other hand, to create a continuous, linear lesion using a single electrode catheter, a number of individual lesions, on the order of forty-five lesions, are required. However, as much as five minutes may be required to position the tip electrode prior to firing it for about one minute. As a result, the lesion creating part of the procedure can be up to and over four hours, not including the requisite time to prepare the patient.

Having thus described preferred embodiments of the present invention, it is to be understood that the above described arrangement and system is merely illustrative of the principles of the present invention, and that other arrangements and systems may be devised by those skilled in the art without departing from the spirit and scope of the invention as claimed below.

I claim:

1. A modular power supply arrangement for a multipolar ablation device, comprising:
    a mother board including:
        a receptacle adapted to receive a module,
        a sine wave oscillator which has an output electrically connected to said receptacle, and
        a feedback control network, which receives input signals from a module insertable in said receptacle, processes the input signals and provides an amplification signal to that module which amplification signal is responsive to the input signals; and
    a module removably connected to said receptacle, said module including:
        at least two RF amplifiers, each of said RF amplifiers being for driving a different pole of the multipolar ablation device in phase with the oscillator output in accordance with the amplification signal from the feedback control network, and
        a plurality of signal sensors for sensing predetermined operating parameters of the multipolar ablation device and providing the input signals to the feedback control network, the plurality of signal sensors being functionally equal in number to said RF amplifiers.

2. The modular power supply arrangement as in claim 1, wherein the receptacle is one of a plurality of receptacles.

3. The modular power supply as in claim 1, wherein said at least two RF amplifiers operate simultaneously.

4. The modular power supply as in claim 3, wherein said at least two RF amplifiers operate at differing levels of amplification in accordance with their respective amplifications signal from the feedback control network.

5. The modular power supply as in claim 1, wherein the input signals to said feedback control network relate to a sensed temperature.

6. The modular power supply as in claim 1, wherein the mother board includes a bidirectional data and address bus communicatively connected to said receptacle.

7. The modular power supply as in claim 6, wherein the bidirectional data and address bus is connectable to a computer configured to provide control signals to the module.

8. The modular power supply as in claim 6, wherein the module is addressed by a signal on the bidirectional data and address bus and wherein the feedback signal for the module is provided to that module on the bidirectional data and address bus.

9. A modular power supply arrangement for a multipolar ablation device, comprising:
    a mother board including:
        a plurality of receptacles each being adapted to receive a module,
        a sine wave oscillator which has an output electrically connected to each of said receptacles, and
        a feedback control network which receives input signals from the module in a respective receptacle, processes the input signals, and provides an amplification signal to that module which amplification signal is responsive to the input signals; and
    at least two modules removably connected to said receptacles, each of said modules including:
        a RF amplifier for driving a particular pole of the multipolar ablation device in phase with said oscillator output in accordance with the amplification signal from the feedback control network, and
        a signal processor for processing predetermined operating parameters of said particular pole of the multipolar ablation device and providing the input signals to the feedback control network.

10. The modular power supply arrangement as in claim 9, wherein each of said at least two modules includes a plurality of RF amplifiers and a functionally equal number of signal processors, each of said plurality of RF amplifiers being for driving a different pole of the multipolar ablation device, each of said equal number of signal processors being for processing the operating parameters of said different pole of the multipolar ablation device.

11. The modular power supply as in claim 9, wherein the RF amplifiers of said at least two modules operate simultaneously.

12. The modular power supply as in claim 11, wherein said RF amplifiers operate at differing levels of amplification in accordance with their respective amplification signals from the feedback control network.

13. The modular power supply as in claim 9, wherein the input signals to said feedback control network relate to a sensed temperature.

14. The modular power supply as in claim 9, wherein the mother board includes a bidirectional data and address bus communicatively connected to said receptacle.

15. The modular power supply as in claim 14, wherein the bidirectional data and address bus is connectable to a computer configured to provide control signals to each of said modules.

16. The modular power supply as in claim 14, wherein each of said modules is addressed by a signal on the bidirectional data and address bus and wherein the feedback signal for an addressed module is provided to that module on the bidirectional data and address bus.

* * * * *